United States Patent [19]

Squires et al.

[11] Patent Number: 5,090,418
[45] Date of Patent: Feb. 25, 1992

[54] METHOD AND APPARATUS FOR SCREENING ELECTROCARDIOGRAPHIC (ECG) DATA

[75] Inventors: Wilber D. Squires, Fountain Valley; John A. Bachman, Dana Point; Bryan L. Laney, Lakewood, all of Calif.

[73] Assignee: Del Mar Avionics, Irvine, Calif.

[21] Appl. No.: 610,979

[22] Filed: Nov. 9, 1990

[51] Int. Cl.$^5$ .......................... A61B 5/0452
[52] U.S. Cl. .................................. 128/702
[58] Field of Search .................. 128/696, 702, 711

[56] References Cited

U.S. PATENT DOCUMENTS

| | | | |
|---|---|---|---|
| 3,799,148 | 3/1974 | Rowen | 128/711 |
| 4,006,737 | 2/1977 | Cherry | 128/711 |
| 4,090,505 | 5/1978 | Mortara | 128/702 |
| 4,316,249 | 2/1982 | Gallant et al. | 128/702 |
| 4,336,810 | 6/1982 | Anderson et al. | 128/702 |
| 4,339,800 | 7/1982 | Woods | 128/702 |
| 4,417,306 | 11/1983 | Citron et al. | 128/702 |
| 4,665,485 | 5/1987 | Lundy et al. | 128/702 |

Primary Examiner—William E. Kamm
Attorney, Agent, or Firm—J. D. Leimbach

[57] ABSTRACT

A time saving automatic screening system for detection, measurement, analysis and plotting of electrocardiographic (ECG) signals employing arrhythmia analysis programs on long term ambulatory (Holter) recordings to assess the ECG signals and categorize the recorded data as either artifact, ventricular ectopic, supraventricular ectopic, unknown or normal and to calculate a level of confidence that the category as chosen is a correct assessment. A system is disclosed that thresholds the occurrences of each category as well as the level of confidence to determine if significant abnormalities have occurred in the recording process, the hearts arrhythmia, or the heartbeat morphology. The method and apparatus disclosed make it possible to identify and screen out entire long term (Holter) ECG recordings containing no significant abnormalities in the hearts arrhythmia or the beat morphology. Thus, the cost of Holter scanning is greatly reduced by reserving for manual scanning only those recordings that contain significant abnormalities in the hearts arrhythmia or the beat morphology.

21 Claims, 13 Drawing Sheets

VE

SVE

ST

UNKNOWN

ARTIFACT

CONFIDENCE INDEX

TIME PERCENT COMPLETE

METHOD AND APPARATUS FOR SCREENING ELECTROCARDIOGRAPHIC (ECG) DATA

BACKGROUND OF THE INVENTION

1. Field of the Invention

This invention relates to the field of electrocardiography and, more specifically, to a method and apparatus for increasing the throughput and lowering the cost in the process of analyzing ambulatory recorded electrocardiographic (Holter ECG) data by automatically scanning patient recordings at high speed and automatically segregating recordings that contain no significant abnormalities from those that contain significant abnormalities. In the case where a Holter recording has significant abnormalities, the invention terminates the automatic analysis based on preset or variable parameters relative to heart arrhythmias, heart morphology, artifact and a level of confidence provided by special algorithms. The preset or variable parameters relative to heart arrhythmias and heart morphologies are based in part on an expanded Lown grade scale. If the high speed analysis indicates that the preset thresholds are exceeded, then the high speed scan is terminated and the recording is relegated to a manual confirm scan using conventional Holter analysis techniques.

The process above can be represented by a medical term known as "Triage TM." Triage TM relates to the medical screening of three types of patients to determine their priority for treatment. In the case of the invention, the scanning of Holter tapes involves three operational modes which operate in sequence but in any sequential order. In this case, the three modes are the fully automatic, manual confirm and the new mode known as Triage TM. In the Triage TM mode where the high speed analysis of a Holter recording can continue automatically where no morphology limits are exceeded, or converts to a manual confirm mode when limits are exceeded, or is terminated early when the recording quality or morphology indicates special manual analysis will be required from the beginning.

2. Description of the Prior Art

In ambulatory monitoring, as normally practiced, the patient wears a device for measuring or sensing physiological or physical variables such as ECG, blood pressure, EEG, posture, etc. These sensed signals are recorded typically on magnetic tape or a solid-state memory. In the case of ECG signals recorded on tape, this is known as a Holter recorder. The recording sessions may last for twenty-four hours or more; thus, the analysis of these tapes is only practical at a higher speed than the recording time, typically 120 to 240 times faster. The signals after analysis on the playback apparatus are typically printed on a high speed laser printer which produces a numerical report with graphical charts and ECG presentations.

Recent developments in high-speed, low-cost computers using Digital Signal Processing (DSP) techniques have made it possible to automatically scan recorded multichannel electrocardiographic data at speeds in the range of 240 to 500 times or higher than the speed at which the data was actually recorded. However, it has remained necessary for most clinical reporting thereon to have skilled personnel scan a tape at high speed, beat by beat, using visual prospective or retrospective techniques to access and correct the computer analyzed data. Using these manual techniques, it is found that typically 30% of the recordings contain no significant abnormalities or artifact; thus, fully automatic analysis is practical with this type of ECG data. The separation of these tapes from the other 70% decreases the amount of skilled technician time in that 30% of the tapes may undergo fully automatic analysis. There still remains the need for scanning recorded ECG data interactively with the technician on a beat-by-beat basis using existing techniques.

An early example of a system for recording and playing back ECG signals is found in Holter et al U.S. Pat. No. 3,215,136 issued on Nov. 2, 1965. A contemporary apparatus for playback and analysis of recorded tapes is described in Cherry and Anderson U.S. Pat. No. 4,006,737 issued Feb. 8, 1977, for "Electrocardiographic Computer." A reissue application of the later patent was filed Apr. 24, 1978, which matured into U.S. Pat. No. Re. 29,921 issuing on Feb. 22, 1979 and a divisional application, Ser. No. 773618, filed Mar. 2, 1977, which matured into U.S. Pat. No. 4,123,785 issuing on Oct. 31, 1978, both being directed to a recorder for cardiac signals. A much improved recorder is described in application Ser. No. 918,698 filed June 23, 1978, and issuing as U.S. Pat. No. 4,211,238, on July 8, 1980, for "Recorder for Ambulatory Monitoring of Electrical Signals," by Shu and Squires. A new method for marking and enhancing CRT screens showing abnormal ECG beats is described in Wong U.S. Pat. No. 4,625,278 issued Nov. 25, 1986.

SUMMARY OF THE INVENTION

The object of the present invention is to provide an automatic analysis of Holter-type recording of ambulatory ECG at a high speed that identifies recordings that do not contain clinically significant abnormalities. It is also the object of this invention to provide an improved ECG system that is capable of improved detection and analysis of high fidelity, analog or digital ECG recordings from either magnetic or solid state media. Another object of this invention to provide a system that can scan recorded electrocardiographic data in either automatic, manual or a combination of automatic and manual modes. Additionally, it is the object of this invention to provide a novel means of automatically scanning, identifying and classifying a plurality of individual patient recordings in sequence by using a batch mode that employs an automatic handling means to sequentially scan individual patient ECG recordings without requiring operator assistance.

Disclosed is a system that consists of a high-speed ECG analyzer which detects heart beats on one, two or three channels using digital techniques for feature vector extraction and noise estimation. Beats having similar feature vectors are grouped into clusters which are then classified to provide for rhythm determination. Confidence testing is performed on all beat and cluster classifications by determining the degree of difficulty in making the respective classifications.

The Triage TM feature of this invention employs three separate operational modes. Typical operation uses an automatic mode having operator adjustable thresholds that are used to terminate a scan when exceeded based on a "Lown" grade criteria. Thresholds are provided for the occurrence of VE's, SVE's, Artifact and unknowns as well as thresholding limits for ST levels and confidence levels. Recordings that do not exceed any of the thresholds are determined to contain no clinically significant abnormalities and are segregated. The recordings that do exceed thresholds may be further analyzed by operator selection of either automatic, manual or Triage TM modes.

DESCRIPTION OF THE PREFERRED EMBODIMENT

Figure 1A:
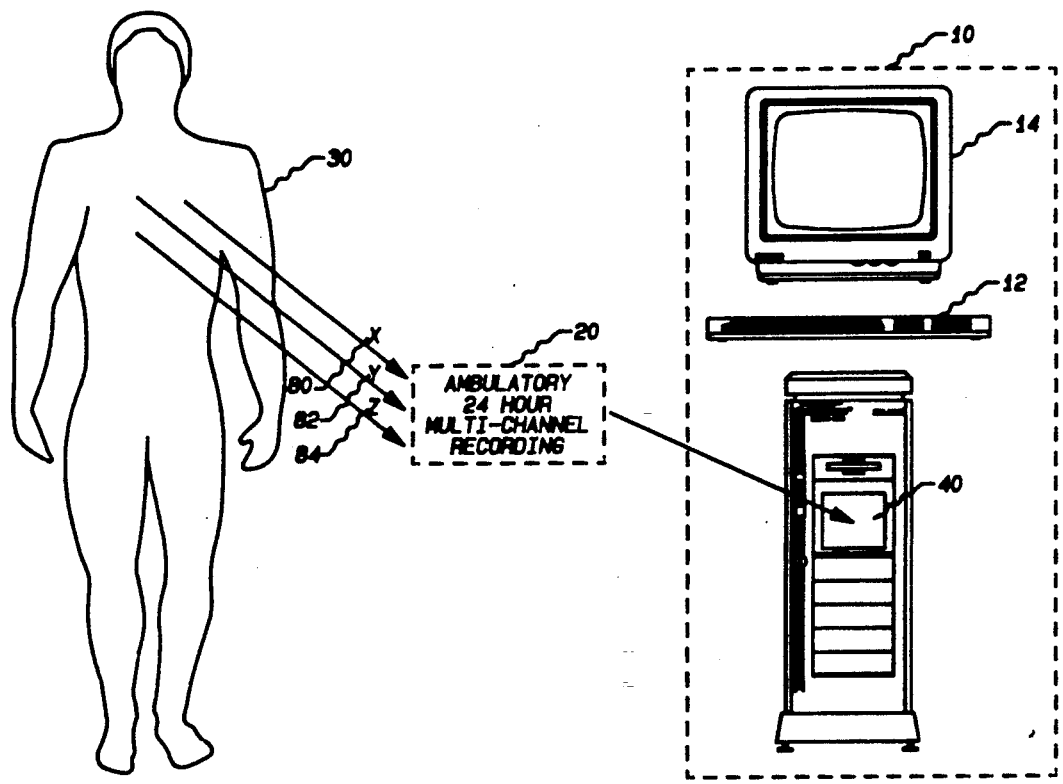
FIG. 1a is a pictorial representation of the Triage TM system and the relevant inputs.

Referring to FIG. 1a, the Triage TM system configuration employs a high-speed, Intel 80486-based, personal computer system 10 providing the speed and power required to execute advanced digital signal processing (DSP) analysis on ambulatory 24 hour multichannel recordings 20. In the preferred embodiment the multichannel recording 20 is made using three channels X, Y and Z (80, 82,84) of ECG input from the patient 30. The computer system 10 includes a high resolution display 14 and a keyboard 12 for operator input.

Figure 2:
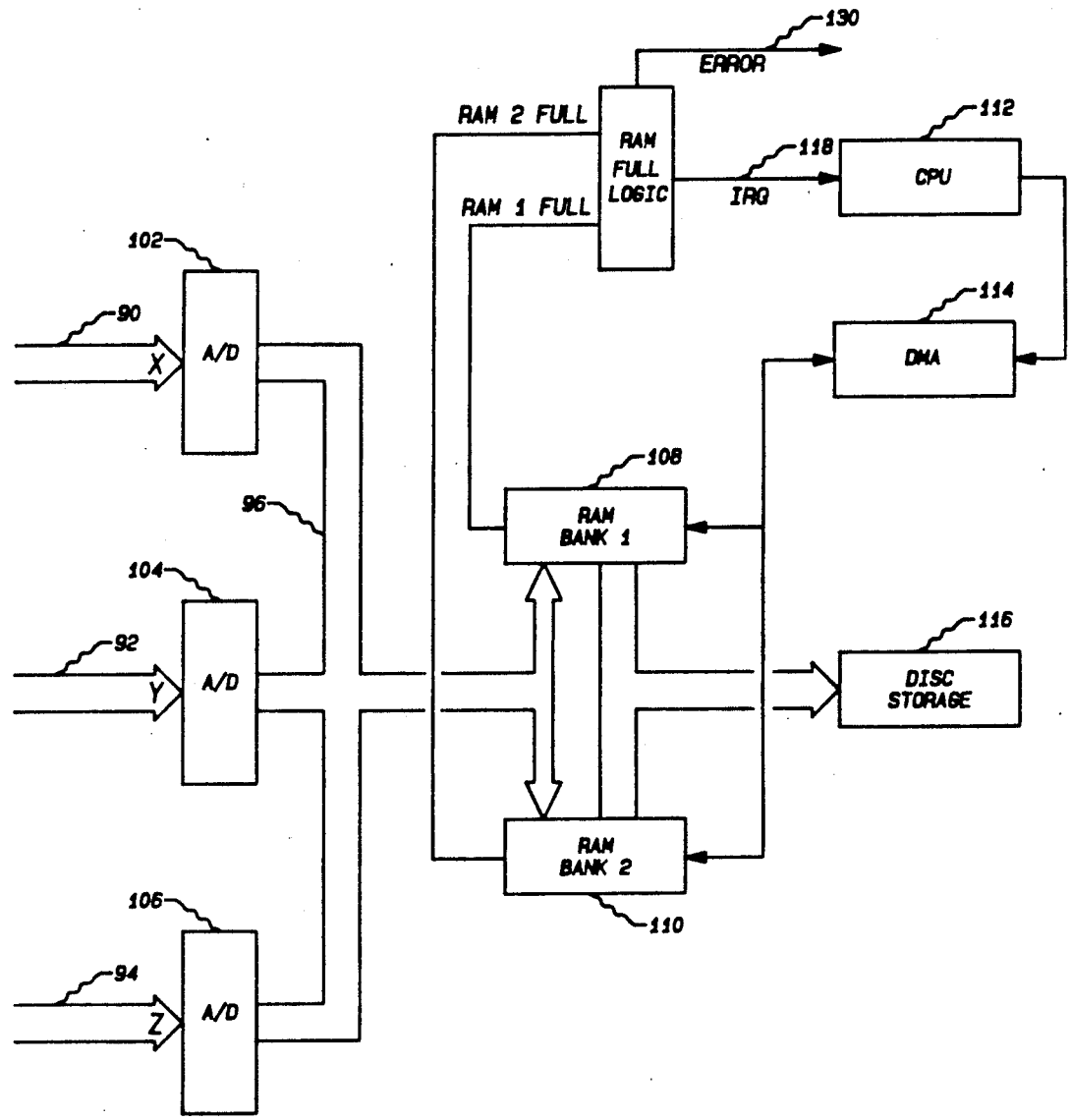
FIG. 2 is a block diagram of the method used to acquire analog ECG data, convert it to digital data and store the digital data on disc.

Referring to FIG. 2, the Triage TM System analyzes up to three channels X, Y, Z (90, 92, 94) of analog Holter (ambulatory) ECG data to detect and identify significant abnormalities in the heart arrhythmia and in heartbeat morphology. In the preferred embodiment, three National Semiconductor ADC0820 high speed A/D convertors (102, 104, 106) are used to convert three channels of analog ECG data X, Y, and Z (90,92,94) into into three digital 8-bit bytes. The converted digital data is stored in either Ram Bank 1 (108), or Ram Bank 2 (110) in 8-bit bytes after being transmitted from the A/D converters to either of the rams along the 8-bit bus (96). Ram Bank 1 (108) and Ram Bank 2 (110) are configured in what is commonly known within the art as a ping-pong arrangement. In this arrangement one of the rams will be written to while the other is being read from. Thus, X, Y, and Z (90, 92, 94) analog ECG data can be converted from analog to digital and stored in one of the rams in three sequential writes of 8-bit bytes, while at the same time, a Direct Memory Access (DMA) transfer can read data out of the other ram. The DMA transfer is performed by DMA Controller (114) to read data out of the ram that is not being written to transfer the data to disc storage (116). The DMA transfer is initiated by the CPU (112) after receiving an interrupt request IRQ (118). The IRQ is generated when either Ram 1 Full (120) or Ram 2 Full (122) are active, which indicates that one of the rams has been written to full capacity and is ready to be read. Only one of the ram full signals may be active at any given time due to the fact that each ram has all of its memory locations written in 45 msec while either ram can be read in 7 msec, therefore the faster reading time prevents the occurrence of the circumstance in which both rams are full. In the event that both ram full signals are active at any given time, an error 130 results and the system terminates operation.

Figure 3:
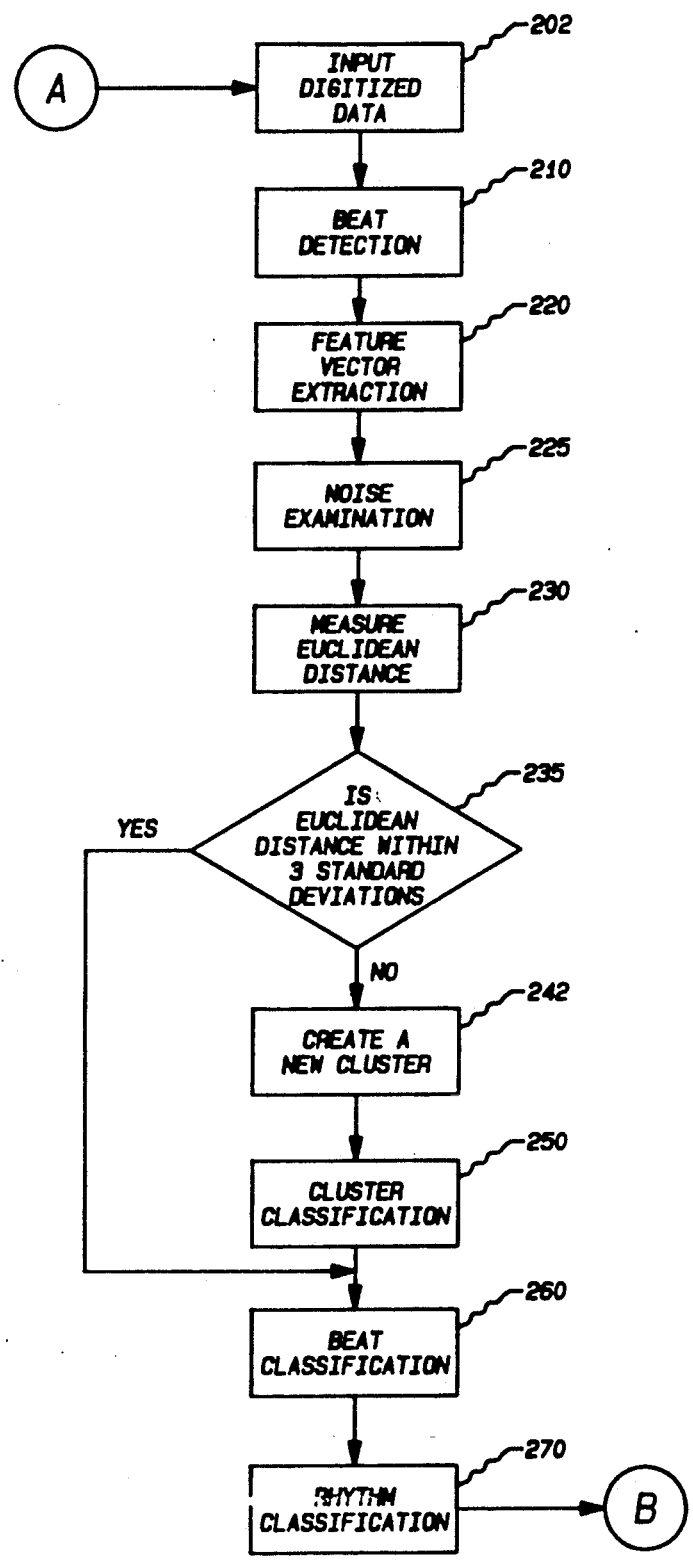
FIG. 3 is a flow chart for the arrhythmia analyzer used in the preferred embodiment of the invention.

As seen in FIG. 3, an arrhythmia analysis and an analysis of the beat morphology and QRS detection are performed by the program modules seen on FIG. 3. Using one, two or three ECG leads, various ventricular and supraventricular arrhythmia are detected. Also detected are assessments of artifact, unknown events and confidence levels. The modules for this analysis perform beat detection 210, feature-vector extraction 220, noise estimation 225, measure euclidean distance 230, euclidean distance within 3 standard deviations (3 std) 235, cluster creation 242, cluster classification 250, beat classification 260 and rhythm classification 270. A discussion of the operation of each module follows. The operating sequence of the analysis is shown in FIG. 3.

Figure 4:
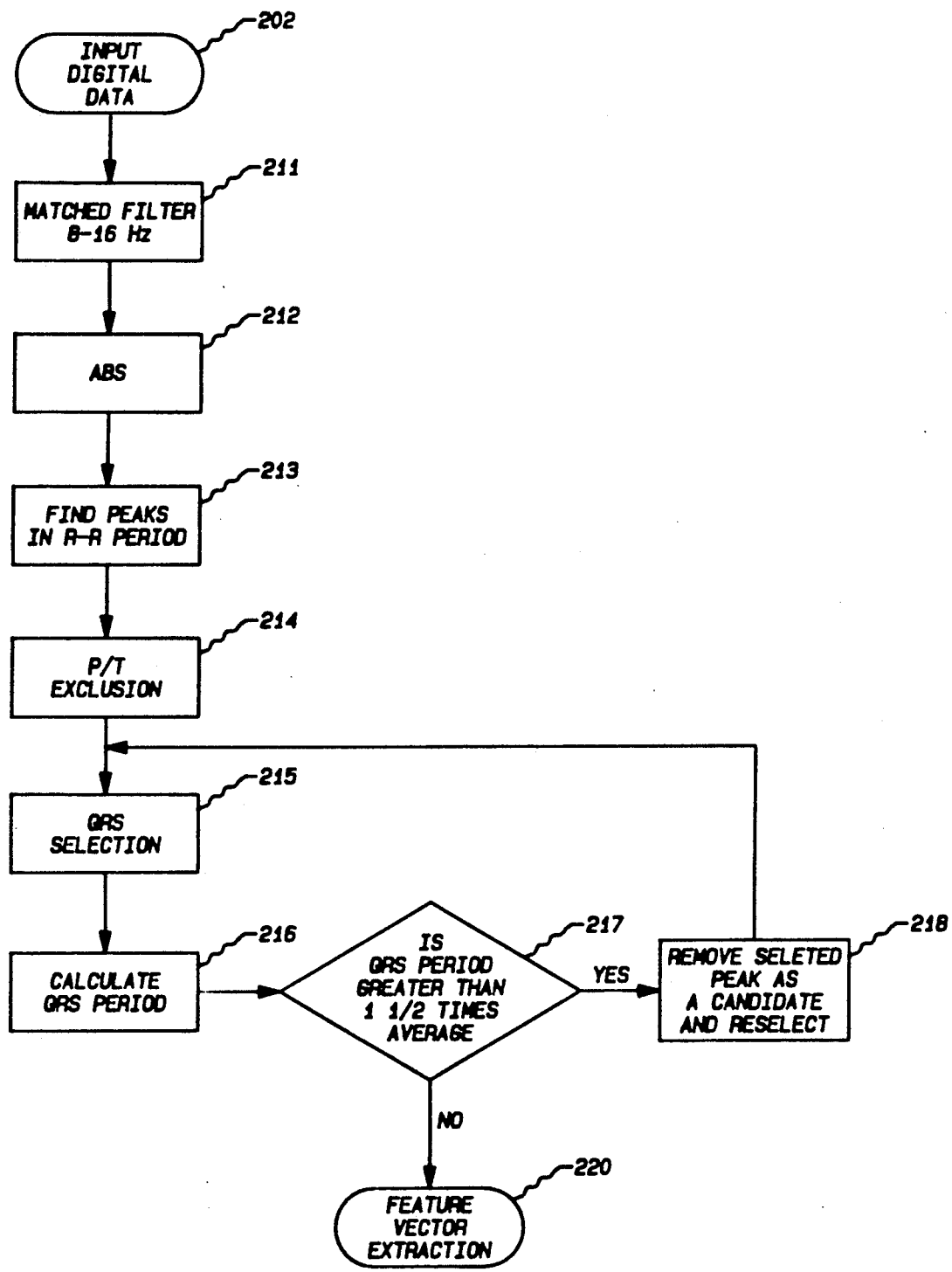
FIG. 4 is a flow chart for the beat detection as used in the preferred embodiment of the invention.

Input digitized data 202 is first tested by Beat Detection 210 for valid heartbeats. A more detailed diagram of the Beat Detection Module can be seen in FIG. 4 to which the following discussion relates. Initially, the ECG data is subjected to a matched filter 211 with an 8–16 Hz bandpass. ABS 212 calculates the absolute value of the filter output of the matched filter 211. The ABS 212 output is then used by Find Peaks 213 to find small peaks. A small peak is defined as a sample point that exceeds the previous sample point by 0.25 mV and is greater or equal to the following sample value. This process is repeated by Find Peaks 213 until all the peaks in an interval equal to the mean R to R interval of the previous peaks are found. The peaks found by Find Peaks 213 are then analyzed by P/T Exclusion 214 to find those peaks that are larger than all the neighboring peaks within a window of 200 to 300 mSec. These larger peaks are then used as candidates. From the candidates found by P/T Exclusion 214, all those which exceed one half the average R wave amplitude are selected as QRS points by QRS Selection 215. The period of the selected QRS points is measured by QRS Period 216. If the duration of the period as found by QRS Period 216 is found to be longer than 1½ times the mean R to R interval then it is determined that a beat has been missed and this will be indicated by QRS Test 217. Upon an indication from QRS Test 217 that a beat has been missed QRS Selection 215 will then select the peak within the mean R-R interval that has the highest amplitude.

Referring again to FIG. 3, Feature vector extraction 220 analyzes the data determined to contain valid heartbeats by the Beat Detection 210 analysis to obtain a vector representation of the heartbeat. A plurality of feature vectors components are extracted to create a multi-dimensional feature vector that characterizes heart beat shape. The multi-dimensional feature vector is created by a modified version of the Karhunen Loeve Transform (KLT) to represent QRS Morphology. This mathematical transformation is applied to detected beats in each channel. The transform characterizes the beat in terms of significant principal components, creating a multi-dimensional feature vector that characterizes the shape of the detected beat. Each QRS complex has samples taken during a 200 millisecond period from a plurality of ECG leads. From these samples QRS pattern vectors are defined.

The KLT is a principle component analysis and that can represent a signal or a waveform by using a finite number of coefficients. A principle component analysis requires that a specific signal or waveform type be modeled in order to create the principle components. An analogy can be made to a Fourier transform in that a Fourier transform can represent a waveform using a finite number of coefficients. However, the base functions of a Fourier Transform are sine functions. Whereas, the KLT creates principle components of a waveform by modeling the waveform to calculate eigenfunctions and using the eigenfunctions as the basis functions.

It is well known that an arbitrary function f(t) can be represented by a series of orthogonal functions say $G_m(t)$ on an interval 0 to a thus, $$f(t) = \sum_{m=0}^{\infty} a_m G_m(t); 0 < t < a$$

Here, the numbers $a_m$ are called the coefficients of this this expansion.

Again making an analogy to a Fourier series expansion, the set of orthogonal functions $G_m(t)$ in a Fourier expansion would be sine functions, and the coefficients $a_m$ would be Fourier coefficients on the interval 0 to $2\pi$. The accuracy to which f(t) can be represented obviously depends on the number of coeficients $a_m$ that are used in the series. The accuracy to which f(t) can be represented for a given number of coeficients will depend on the set of orthogonal functions $G_m(t)$ that are used.

The concept of the Karhunen-Loeve transform is also known as a principle component transform, is that a set of orthogonal functions is selected by examining the function to be represented. Thus, the set of derived functions will most accurately represent the original function for any given number of coefficients.

Figure 12A:
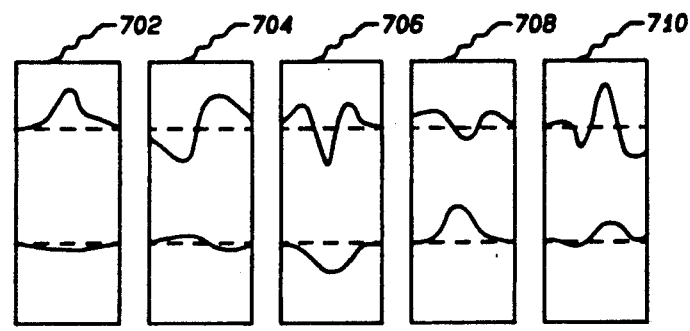
FIG. 12a is a pictorial representation of the eigenvectors used as the principle components in modeling QRS waveforms.
Figure 12B:
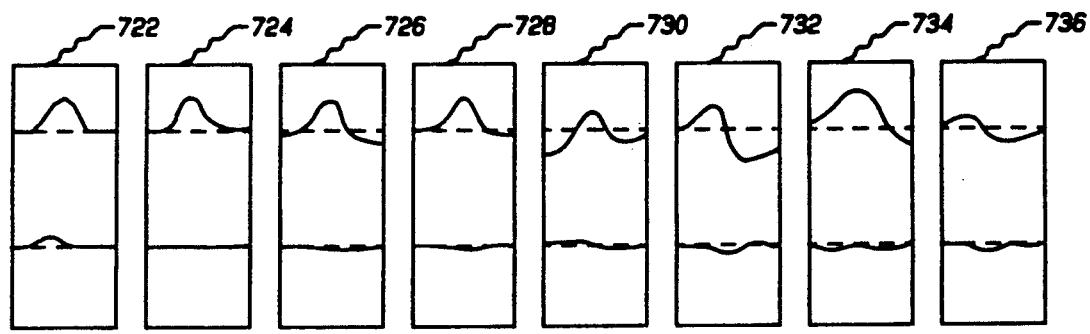
FIG. 12b is a set of sample input QRS waveforms.
Figure 12C:
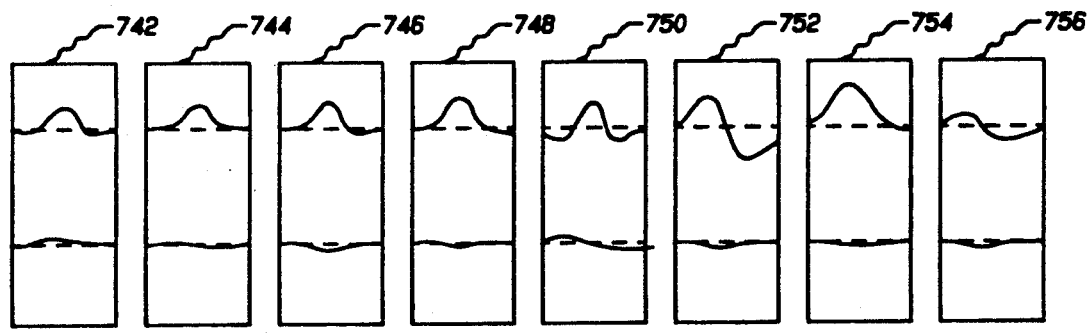
FIG. 12c are the output waveforms using the principle components to model the sample set of of QRS waveforms.

In the preferred embodiment, the function to be represented is the ECG complex in an interval of 200 milliseconds as shown in FIG. 12b (722, 724, 726, 728, 730, 734 and 736). The set of orthogonal functions used are the first five order eigenfunctions (702,704,706,708,710) as seen in FIG. 12a. The reconstruction of the ECG complex shown in FIG. 12c (742, 744, 746, 748, 750, 752,754, and 756) is accomplished using the eigenfunctions (702,704,706,708,710) of FIG. 12a. Assuming that the waveform is not unduly noisy, the five principal components (702,704,706,708,710) establish a comprehensive base from which virtually any ECG signal can be analyzed. The analysis is accomplished by correlating the components of an analyzed input signal with the comprehensive base that is generated from the five principal components that are used as basis functions, similar to the manner in which sine functions are used as basis functions for Fourier transforms. The comprehensive base is generated prior to running the arrhythmia analysis and is permanently stored in the system in the preferred embodiment. By having a comprehensive base built upon ECG basis functions, ECG analysis can be accomplished by correlating the components of an input waveform in real time.

The KLT residual is the amount of energy in the original ECG which is not contained in the resultant KLT transformed values. The KLT residual is one of several indicators of noise level used by the Noise Estimation Module 224. Noise is a major source of error in all arrhythmia analysis programs. The KLT's ability to separate noise is directly relational to the number of coefficients that are used. The larger the number of coefficients the better the noise separation.

The measured Euclidean distance 230 takes the results of the feature vector extraction 220 and measures the squared euclidean distance between the beats feature vectors and the center of each cluster.

In the preferred embodiment a beat is considered part of a cluster if the measured euclidean distance 230 is within three standard deviations. The measurement threshold used to approximate three standard deviations in the preferred embodiment is 2NF+4. Here, NF is the number of features which in the preferred embodiment is equal to 5. Three standard deviations is a measure that includes 98% of the features of beats within a cluster.

Cluster Creation 240 is responsible for the generation of clusters in accordance with beat morphology and confidence levels. Cluster Creation 240 is a means for creating clusters by grouping the heart beats having similar feature vectors. Beats of similar shape have similar feature vectors. As each new feature vector is created, it is compared with clusters of previously existing vectors. Clusters are compared by Measure euclidean distance 230 squaring the euclidean distance of the vector and measuring the distance between the recently created vector and each existing cluster. If the Euclidean distance of a vector is not within three standard deviations of an existing cluster, then this is so indicated by Standard Deviation 235 and Cluster Creation 240 creates a new cluster. If a vector's euclidean distance to any existing cluster is within three standard deviations of an existing cluster then the vector is placed within that cluster.

Once created, a cluster is classified by the Cluster Classification 250 as Normal, VE, SVE or Unknown, depending on characteristics of the beats comprising the cluster. Beat Classification 260 then classifies and labels the beat. Generally the beat is classified the same as the matching cluster classification. One exception is a beat which matches a normal cluster is called an SVPB if it is premature by 20% or more, otherwise it is classified as normal. In the preferred embodiment the criteria used for determining beat type is the beat annotation label as shown in Table 1.

TABLE 1

| Label | Beat Types<br>Beat Type Criteria |
|---|---|
| o Normal | Normal cluster not meeting SVPB prematurity criteria. |
| V Ventricular | Abnormal cluster that is premature, or |

TABLE 1-continued

| Label | Beat Types Beat Type Criteria |
|---|---|
| Ectopic (VE) | on time, or late compared to the current mean R-R interval. |
| S Supraventricular Premature | Beat (SVPB) Normal cluster having beats (SVPB) premature by 20% or more. |
| Q QRS of unknown type | Beat does not fit criteria for normal or abnormal or is too noisy to cluster. |
| ? Learning | First 50 detected beats used to establish normal cluster and initial R-R interval. |
| O Other | Miscellaneous categories such as pacer, aberrantly conducted SVE's, etc. May be labeled in post-analysis review. |

The Rhythm Classification 270 is the sequence and interval of the heartbeats and it is used to detect and label various arrhythmia episodes. In the preferred embodiment of the invention, the sequence and interval criteria used to describe the arrhythmia episodes are described in Table 2 below.

TABLE 2

| Arrhythmia | Arrhythmia Episodes Criteria |
|---|---|
| Ventricular Bigeminy* | Ventricular extrasystoles occurring alternately with other beats beat sequence VxVxV |
| Ventricular Trigeminy* | Ventricular extrasystoles occurring alternately with other beats Beat sequence VxxVxxV |
| Ventricular Couplet | Two ventricular beats with a heart rate of greater than 95 bpm Beat sequence xVVx. |
| Ventricular Triplet | A sequence of three ventricular beats with a heart rate greater than 95 bpm Beat sequence xVVVx. |
| Ventricular Tachycardia | A rapid succession of four or more ventricular eptopic beats occurring consecutively in which there is a three beat average rate of 95 bpm or greater. |
| Idioventricular Rhythm (IVR) | An arrhythmia of three or more sequential ventricular ectopics with a three beat average heart rate of less than 50 bpm. |
| Bradycardia | A slowness of the heart beat, here defined as three beat average heart rate that is less than 45 bpm with the three intervals between beats constituting the bradycardia and the previous beat being greater than 1500 mS. |
| SV Tachycardia | A 3-beat average heart rate less than 80 bpm with all three beats being at least 20% premature. |
| Pause | Where the interval between two consecutive R waves is greater than 2 seconds. |
| 2 R-R | The interval between two consecutive R waves is twice the previous interval plus or minus 25%, or twice the following interval plus or minus 25%. |
| Atrial Fib or Flutter | A complex computation based on prematurity produces a number for each beat. These numbers are averaged over 64 beats (excluding VE's). Atrial fibrillation is declared if the average is greater than 100 bpm and heart rate is greater than seventy (70). |
| SVE Single | Beat sequence "xSx." |

LEGEND
V = ventricular ectopic
S = supraventricular ectopic
x = any other type beat
*Taken in a literal sense, bigeminy and trigeminy would define groupings of two and three pairs respectively. However, after repeated use these terms have come to signify the occurrence of two, three and four beats. It is in this sense that these terms are used herein.

Figure 5:
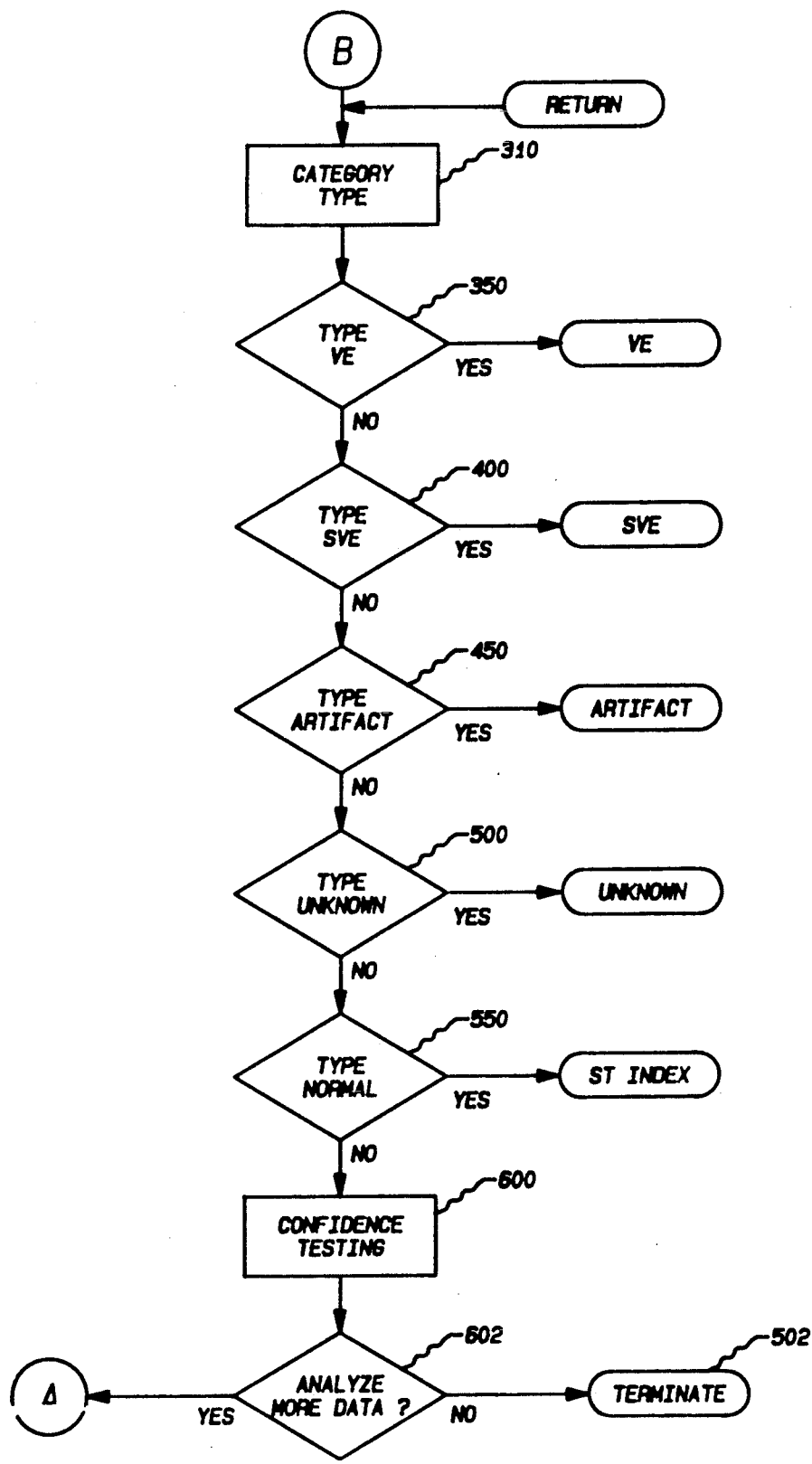
FIG. 5 is a flow diagram for the main routine of the Triage TM thresholding.

Referring to FIG. 5, the Arrhythmia analyzed data is categorized by category type 310 as being either VE 350, SVE 400, artifact 450, unknown 500, or normal 550. Once the arrhythmia analyzed data's proper category is determined processing then branches to the appropriate routine. Confidence testing 600 is performed on all type categories after processing for that particular category has been completed. After confidence testing is performed, a decision is made whether to analyze more data 602. This decision can be based on a variety of factors, one of them being the completion of testing. In the preferred embodiment a completion of testing would generally occur at about 20 hours into a 24 hour test. A decision that testing is complete would yield a negative answer to analyze more data 602, while if more testing still had to be done would yield a positive answer to analyze more data 602.

Figure 6:
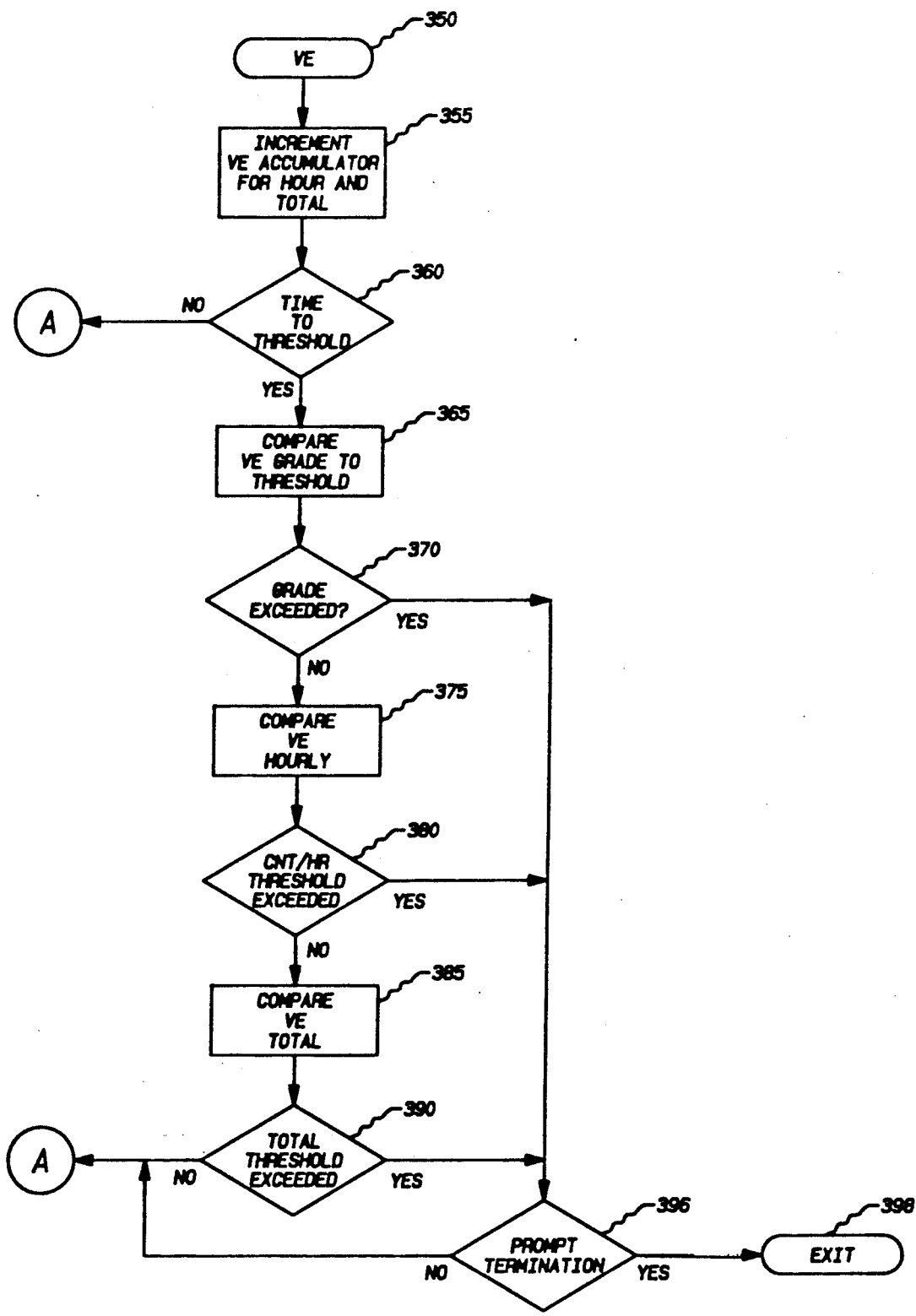
FIG. 6 is a flow diagram of the method used to threshold VE occurrences.

Referring to FIG. 6, data assessed to be in the VE category causes the VE accumulator 355 to be incremented. The VE accumulator 355 actually consists of two accumulators, one to count the occurrences of VE's during the last hour and another to count the occurrences of total VE's. Once VE accumulator 355 counts the occurrence of a VE, the Triage TM threshold timer 360 is checked to determine whether thresholding will take place. In the preferred embodiment the Triage TM timer is preset to 10 minutes of patient time although various presets may possibly be used. In the event that the Triage TM timer has not elapsed, processing returns to retrieve more arrhythmia analyzed data. However, when the Triage TM timer has elapsed the VE grade as determined by the arrhythmia analyzer is compared with the preset grade threshold 365. The VE grade may be set to any of the values in Table 3. A decision is then made based on whether the grade has been exceeded 370. If the VE grade has been exceeded then the prompt termination 396 box is executed. When prompt termination 396 is activated the operator has three choices: (1) return to Triage TM; (2) enter confirm mode; and (3) terminate the program.

TABLE 3

(1) no VE activity
(2) between one and 30 VE events within the span of sixty minutes
(3) more than 30 VE events in the span of sixty minutes
(4) a VE pair (two consecutive beats being classified as VE) occuring
(5) an intraventricular run of more than three VE's occuring with a heart rate of less than 95 beats per minute
(6) a VE triplet (three consecutive beats classified as VE with a heart rate of more than 95 beats per minute occuring
(7) a VT run of 4 or more VE's In the event that the VE grade selected from Table 3 is not exceeded, compare VE hourly 375 checks the VE occurrences within the last hour as compared to the preset threshold to see if the hourly occurrence threshold has been exceeded. CNT/HR Threshold Exceeded 380 prompts termination 396 from the operator in the event the VE hourly threshold is exceeded, as discussed above. Compare VE total 385 checks the total numbers of VE occurrences against the threshold for the total number of occurrences if the threshold for hourly occurrences has not been exceeded. Total threshold exceeded 390 will route system analysis to prompt termination 396 if the comparison of total VE 385 occurrences exceeds the preset threshold and return operation to retrieve more arrhythmia analyzed data if the threshold has not been exceeded.

Figure 7:
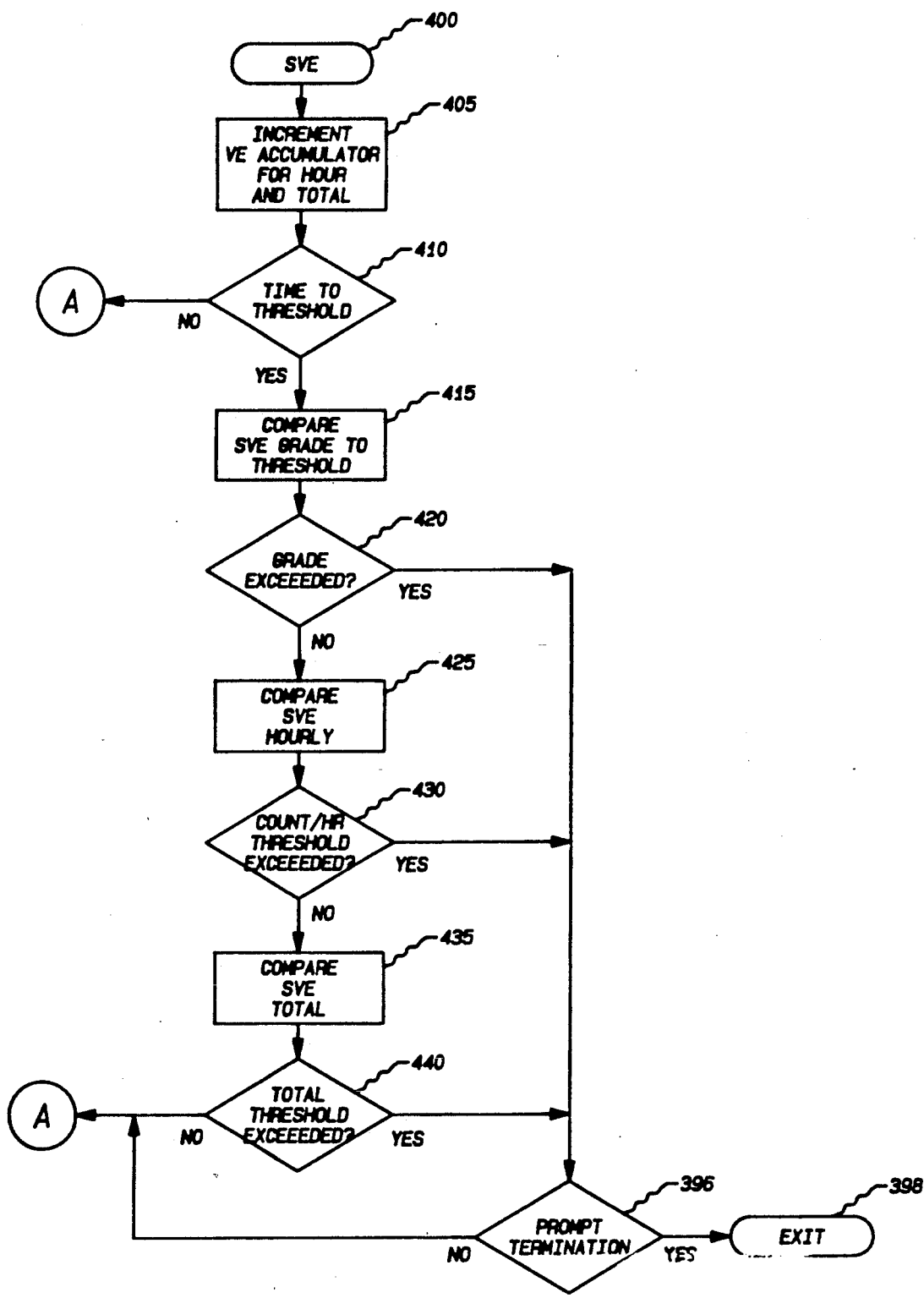
FIG. 7 is a flow diagram of the method used to threshold SVE occurrences.

Referring to FIG. 7, data that the arrhythmia analyzer has assessed to be of the SVE category is used to increment the SVE Accumulator 405 which will accumulate both occurrences of SVE's during the last hour and occurrences of total SVE's in the same manner as discussed for VE's above. Once SVE accumulator 405 counts the occurrence of a SVE the Triage TM threshold timer 410 is checked to determine whether thresholding will take place. In the preferred embodiment the Triage TM timer is preset to 10 minutes although many presets can be used. If the Triage TM timer has not run, processing returns to retrieve more arrhythmia analyzed. However, if the Triage TM timer has elapsed then Triage TM thresholding will take place. Once thresholding begins, the SVE grade as determined by the arrhythmia analyzer is compared with the preset threshold 415. The SVE grade may be set to any of the values in Table 4. Grade exceeded 420 then makes a decision based on the result of compare SVE grade to threshold 415. If the SVE grade has been exceeded then the prompt termination 396 box is executed. When prompt termination 396 is activated the operator has three choices: (1) return to Triage TM; (2) enter confirm mode; and (3) terminate the program.

TABLE 4

(1) no SVE activity
(2) 1 to 30 SVE's in a sixty minute span
(3) more than 30 SVE's occuring within an hour
(4) a SVE pair
(5) TBD
(6) SVT run of three to five
(7) SVT run of more than five
(8) pause If the SVE grade as selected from Table 4 is not exceeded, then analysis proceeds in a fashion similar to that of VE occurrences. Compare SVE hourly 425 compares the SVE occurrences within the last hour against the preset threshold. If the hourly occurrence threshold has been exceeded then CNT/HR Exceeded 430 prompts termination 396 from the operator as discussed above. Alternatively, if the threshold for hourly occurrences is not exceeded compare SVE total 435 checks the total numbers of SVE occurrences against the threshold for total occurrences. Total threshold exceeded 440 will route system analysis to prompt termination 396 if the total number of SVE occurrences exceeds the threshold and return operation to retrieve more arrhythmia analyzed data if the threshold has not been exceeded.

Figure 8:
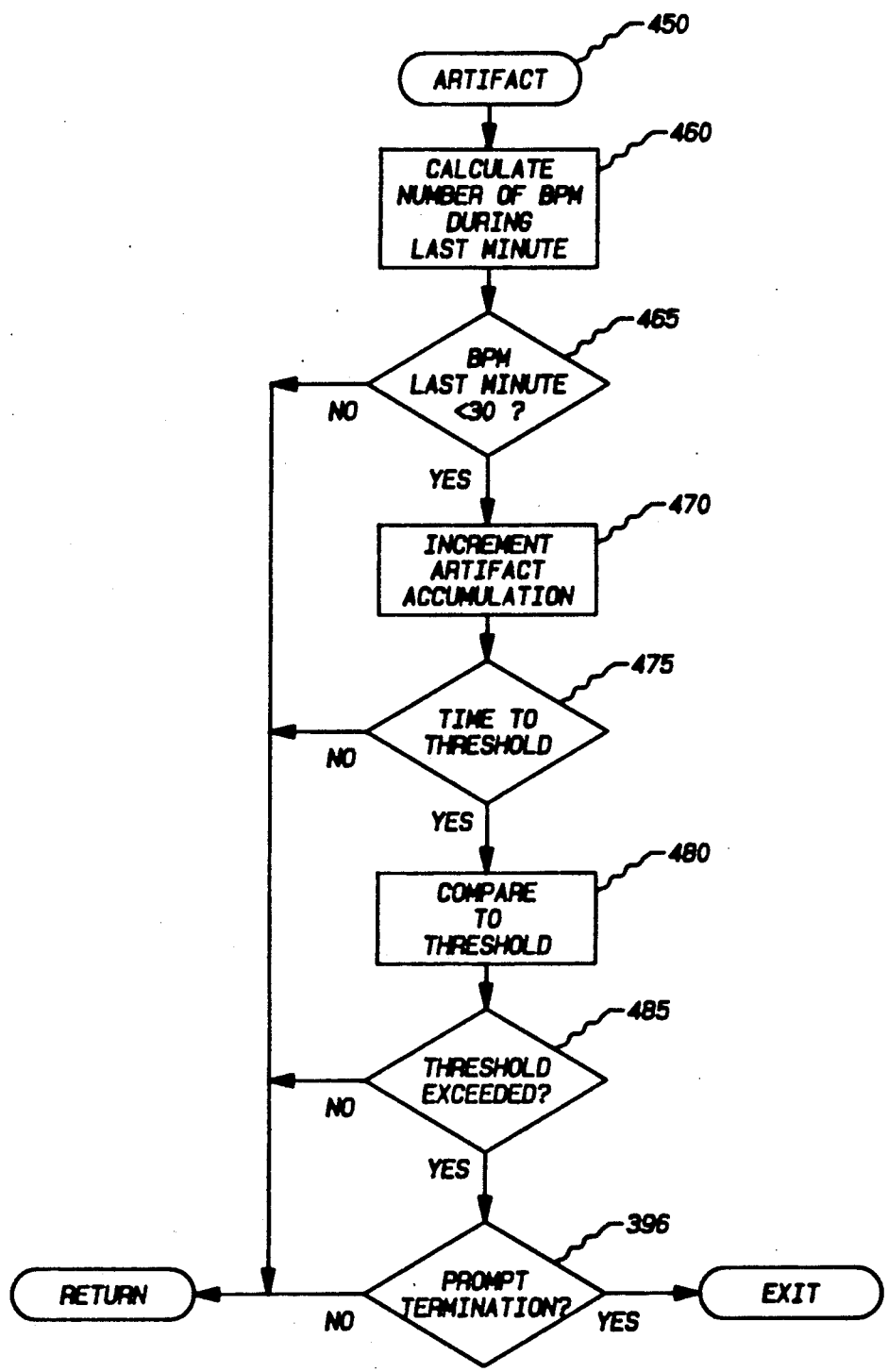
FIG. 8 is a flow diagram of the algorithm used to threshold the occurrence of artifact.

As shown in FIG. 5, once data is classified as artifact by the arrhythmia analyzer the system then begins a determination of whether an artifact minute should be accumulated. Referring to FIG. 8 artifact 450 calculates the cumulative number of artifact minutes by calculating the number of beats per minute during the last minute 460. If the bpm in the last minute is less than 30 465 then the artifact accumulator 470 is incremented prior to checking time to threshold 475. If the threshold timer has expended then compare to threshold 480 checks the present value of the accumulator against the preset value for the Triage TM threshold for artifact. If the threshold is exceeded 485 then the system prompts termination 396 from the operator.

Figure 9:
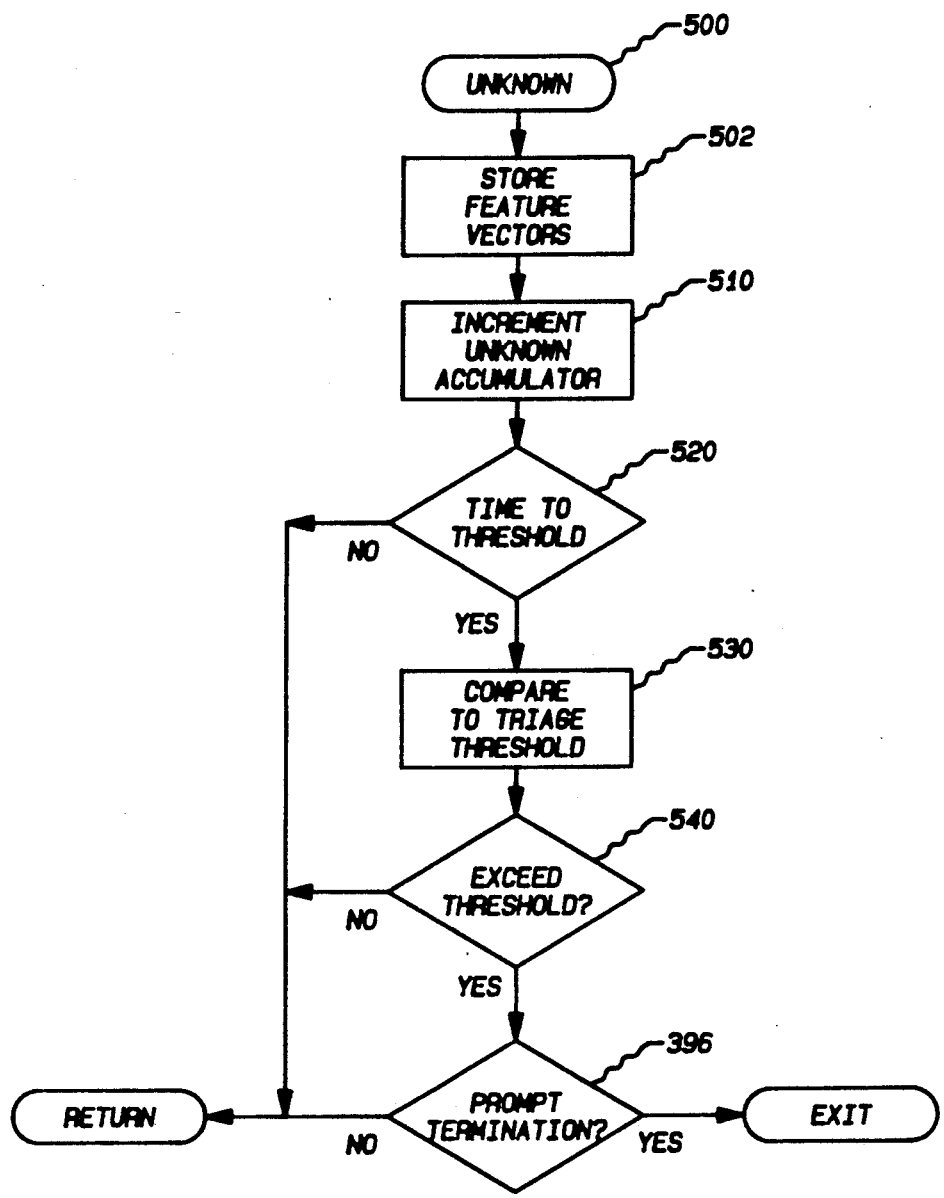
FIG. 9 is a flow diagram of the algorithm used to threshold the occurrence of unknowns.

As shown in FIG. 5 data that has been categorized as unknown by the arrhythmia analysis is routed to the analysis for unknown data. Referring to FIG. 9, store feature vectors 502 retains the morphology of the unknown beat. The occurrence of the unknown is then used to increment the unknown accumulator 510. Operation then checks to see if its time to threshold 520 and if not returns to retrieve more arrhythmia analyzed data. If time to threshold 520 is true then the unknown accumulator is compared to the Triage TM threshold 530. If the threshold is exceeded then the system prompts termination 396, otherwise operation returns to retrieve more arrhythmia analyzed data.

Figure 10:
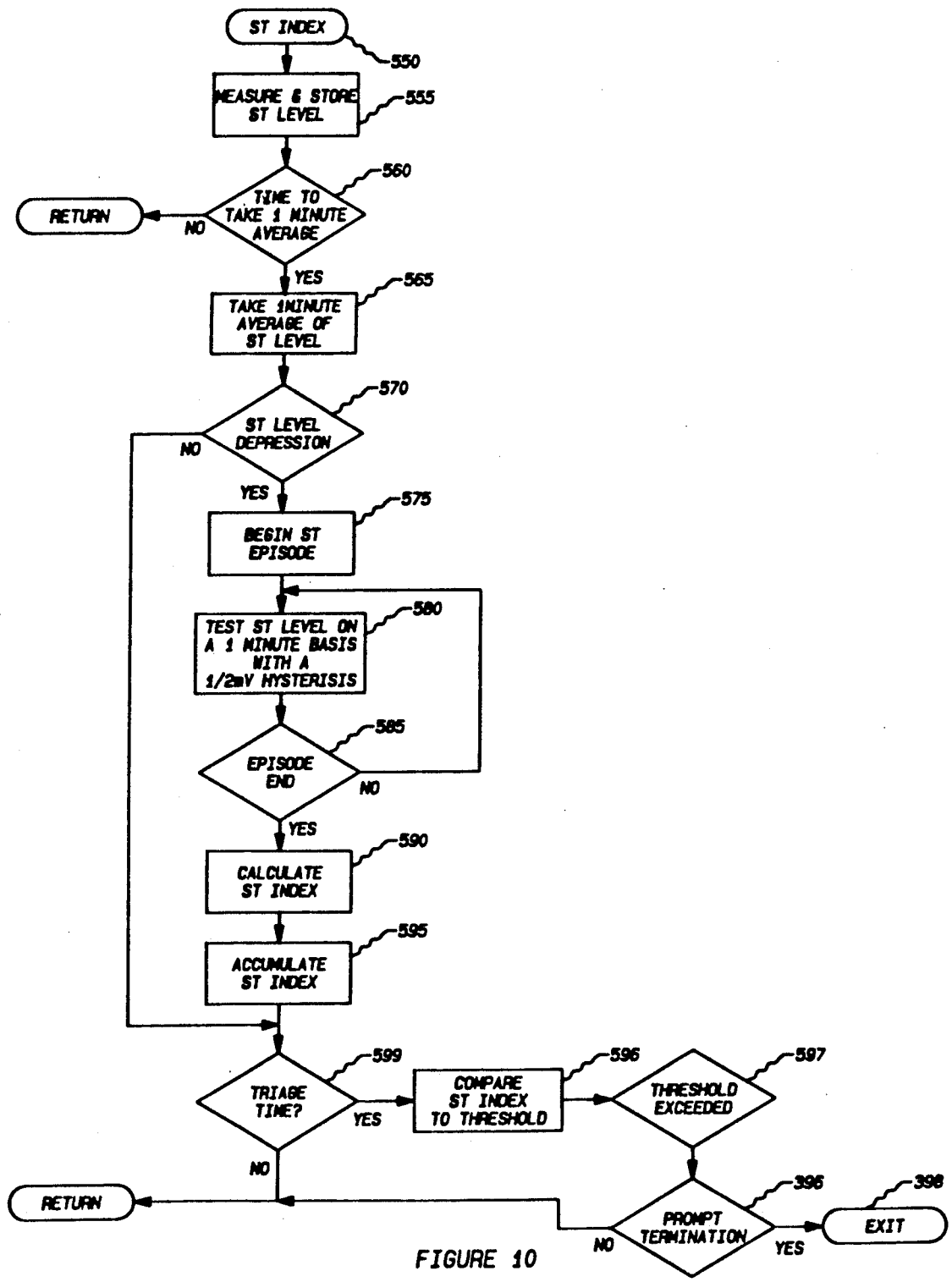
FIG. 10 is a flow chart demonstrating the calculation of ST indexes.

Referring to FIG. 5, data that has been given the category type 310 of normal will be directed by type normal 550 to have the ST index calculated. As seen in FIG. 10, the ST Indexing 550 tracks the occurrences of ST episodes. An ST episode occurs when the ST level experiences a 0.1 millivolt depression, which if witnessed on an ECG graph would be depressed one millimeter. There is operator adjustable hysteresis used in the calculation of the end point of the ST episode. Thus, the duration of an ST episode is determined both by the particular ECG recording and by the operator preset hysteresis. The ST index is defined as the amplitude of the depression multiplied by the length of the episode. All beats determined to be normal by the arrhythmia analyzer have their ST Level measured and stored 555. Time to average 560 a decides either to take the average of the ST Level over the last minute or to return processing to retrieve more arrhythmia analyzed data. If one minute has not past since the last ST level averaging time to average 560 returns processing to the arrhythmia analyzer to retrieve more data. If one minute has past since the last ST level averaging time to average routes processing to average ST level 565. Average ST Level 565 takes the sum of the ST levels computed by measure and store the ST level 555 over the last minute and averages the ST level over that minute. Once the ST level has been averaged ST level depressed 570 checks the averaged level against 0.1 millivolt. If the averaged ST level does not show at least a 0.1 millivolt depression then ST level depressed 570 directs the system to interrogate the Triage TM timer 599 in order to decide if the ST index should be compared to the Triage TM threshold. If ST level depressed 570 . finds a 0.1 millivolt depression in the one minute averaged ST level, then begin ST episode 575 declares that an ST episode has begun by the detection of an ST depression. Processing will the test ST level on a one minute basis 580 to check the ST level for a level that is considered normal. In the preferred embodiment a hysteresis of 0.05 millivolt is used in conjunction with a normal level to verify the return of ST level to normal. Once the ST level has returned to a normal level episode end 585 routes system operation to calculate the ST index 590. The ST index is defined as the absolute value of the ST depression multiplied by the duration of the episode. Accumulate ST index 595 sums all the ST indexes after the ST index is accumulated. Once the ST index has been accumulated the Triage TM timer 599 is then interrogated. If the Triage TM timer has not been expended the system then returns to retrieve more arrhythmia analyzed data. If the Triage TM timer has been expended, then the accumulated ST index is compared to a Triage TM threshold value 596. ST index threshold 597 routes the systems operation to prompt termination 396 if the Triage TM ST index threshold 596 is exceeded. Prompt termination 396 then prompts the operator as discussed above. If the Triage TM ST index threshold 597 has not been exceeded then threshold exceeded will return program operation to retrieve more arrhythmia analyzed data.

Figure 11:
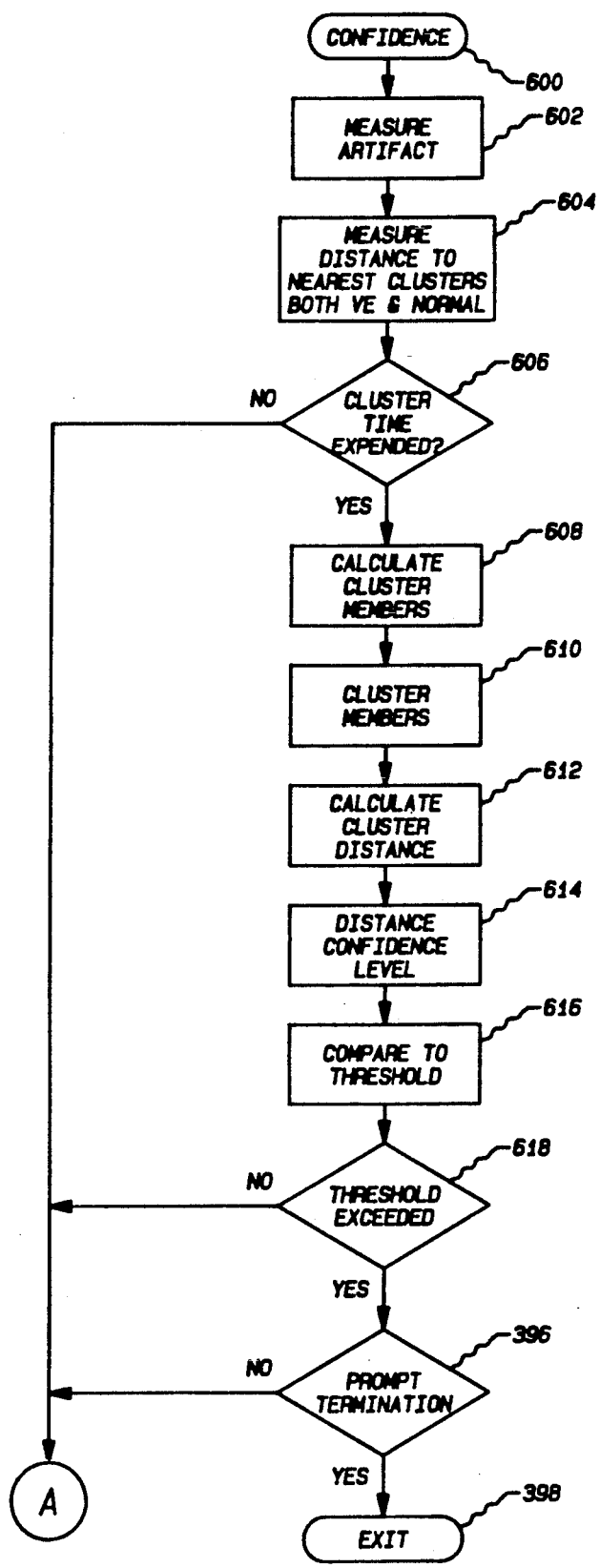
FIG. 11 is a flow chart showing the calculation of confidence levels.

All arrhythmia analyzed data has confidence levels formed. As shown in FIG. 5 the confidence testing 600 is not a decision but a function that is performed on all data. Two confidence levels are assessed in the preferred embodiment. The first for each beat to determine whether it belongs to a particular cluster. The second confidence level is used in a determination that the present selection of clusters is a valid cluster selection. There are several factors used in determining the confidence level. Referring to FIG. 11, measure artifact 602 determines the amount of artifact contained within each beat. The artifact is used in the measure of confidence. Next measure distance 604 places a confidence level on euclidean distances to the nearest VE clusters and to the nearest normal clusters. These confidence levels for each analyzed beat are then immediately stored. Cluster timer expended 606 then checks the time period since the last cluster confidence level determination. In the preferred embodiment, the cluster timer expended is preset to 10 minutes, although different presets can be used in various embodiments. If the cluster timer expended 606 interrogation shows that the preset time has not past, then operation proceeds back to retrieve more arrhythmia analyzed data. Once an interrogation of cluster timer expended 606 shows that the preset period has lapsed then calculate cluster members 608 sums the number of beats associated with each cluster. Confidence levels are then assigned based upon the number of cluster members 610. Calculate cluster distance 612 determines the euclidean distance between the various clusters. The calculated distance is then used by the distance confidence level 614 to assign another confidence level to the clusters. All the above confidence levels are scaled and summed together as each is calculated. The accumulated confidence level is then compared to the Triage TM confidence threshold 616. If the result of the comparison shows the threshold exceeded then the operator is prompted for termination 396 as discussed above. If the confidence threshold is not exceeded then the next piece of arrhythmia analyzed data is input and analysis continues.

Figure 13:
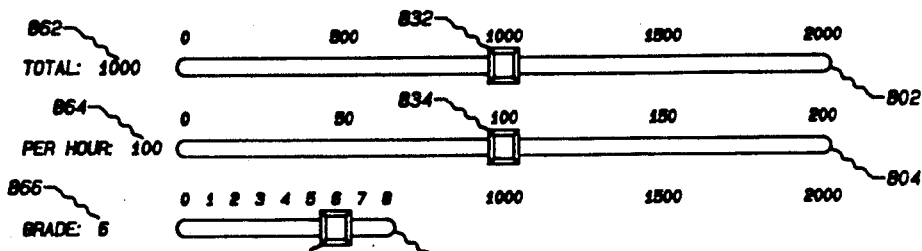
FIG. 13 is a pictorial representation of a high resolution display of the slider switches used to set threshold values.
Figure 13:
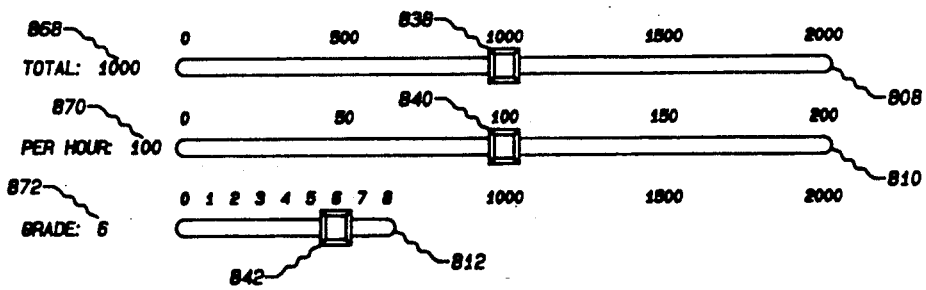
Figure 13:
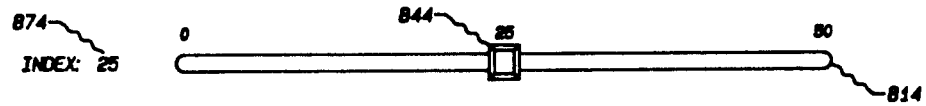
Figure 13:
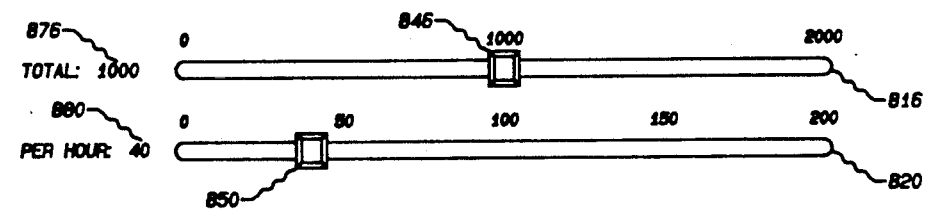
Figure 13:
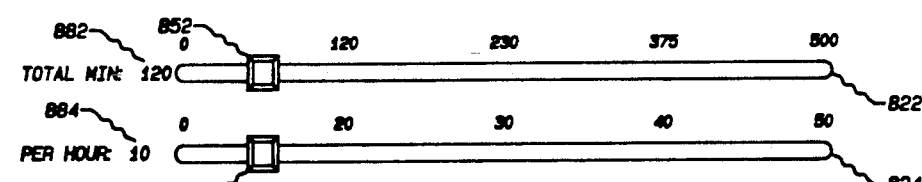
Figure 13:
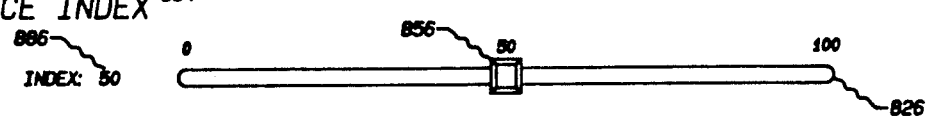
Figure 13:
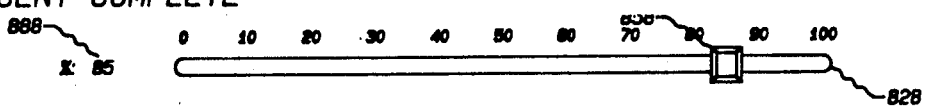

Referring to FIG. 13, predetermined thresholding values are preset by adjusting any of a plurality of graphical slider switches. The presentation of the graphical slider switches comes at the request of the operator and has the appearance of a group of slider switches that may be adjusted by the operator using the mouse or cursor keys to move the switches to the desired value. In the preferred embodiment the present accumulation of each category is displayed on the slider switch display along with the present Triage TM threshold. As analysis progresses the present accumulations are incremented for each occurrence of a respective category. If any of the threshold values are exceeded, analysis will stop, and the operator will be prompted for action as discussed above. The user may view the data and decide whether to terminate analysis, reset the thresholds and continue, or to change to a confirm mode analysis. A confirm mode is where the user is asked to validate or change what the analyzer would call a cluster when a new cluster is created.

As seen on FIG. 13, graphical slider switches (802, 804, 806, 808, 810, 812, 814, 816, 820, 822, 824, 826, 828) control the Triage TM thresholds by allowing for operator adjustment via computer keyboard or mouse input. Each of the thresholding switches is adjusted by the operator moving the bar on the slider switch. The slider switches for thresholding the occurrence of VE's per hour 804 and SVE's per hour 810 can be independently preset to anywhere between 0 to 200 occurrences per hour by moving the VE per hour slider bar 834 or the SVE per hour slider bar 840. The present value for the VE per hour threshold 864 is displayed to the left of the VE per hour slider switch 804, while the present threshold for SVE's per hour 870 is shown to the left of the SVE per hour slider switch 810. In a similar manner the slider switch for thresholding the occurrence of total VE's 802 and total SVE's 808 can each be independently preset from anywhere from 0 to 2000 occurrences by adjusting the total VE slider bar 832 and the total SVE slider bar 838 respectively. The present threshold for total VE's 862 and the present threshold for total SVE's 868 are displayed to the left of their respective slider switch. The thresholds for VE and SVE grade are controlled by the VE grade slider switch 806 and the SVE grade slider switch 808 being preset by the VE grade slider bar 836 and the SVE grade slider bar 842 respectively Again, the present value of the presets shown to the left of the slider switches. Proceeding in a similar fashion, the ST index slider switch 814 is preset by the ST index slider bar 844 which is displayed by the present ST index threshold display 874. The occurrence of unknown beats is thresholded by presetting the total unknown slider switch 816 and the unknown per hour slider switch 820 with respective slider bars 846, 820. The selected preset is displayed to the left of the slider switches by the total unknown threshold display 876 and unknowns per hour threshold display 880. Artifact is thresholded by presetting the artifact total minute slider switch 822 and the artifact per hour slider switch 824 by adjusting the artifact total minute slider bar 852 and the artifact per minute slider bar 854 to yield the display of the present threshold setting for artifact total minutes 882 and the display for the threshold preset for artifact per hour 884. The confidence level index is thresholded by adjusting the confidence index slider switch 826 to a scaled value of anywhere between 0 and 100 by adjusting the confidence slider bar 856 to the desired preset value which is then displayed by the confidence threshold display 886. Finally, the running time of the test can also be thresholded by adjusting the percent complete slider switch 828 to the desired value by adjusting the confidence slider bar 858. The percentage at which the system will automatically stop operation is then displayed on the percent complete threshold 888. Thus, it is possible for the operator to determine the levels at which the system will automatically decide that the recording contains no significant abnormalities and may therefore be excluded from the requirement of manual analysis.

Figure 1B:
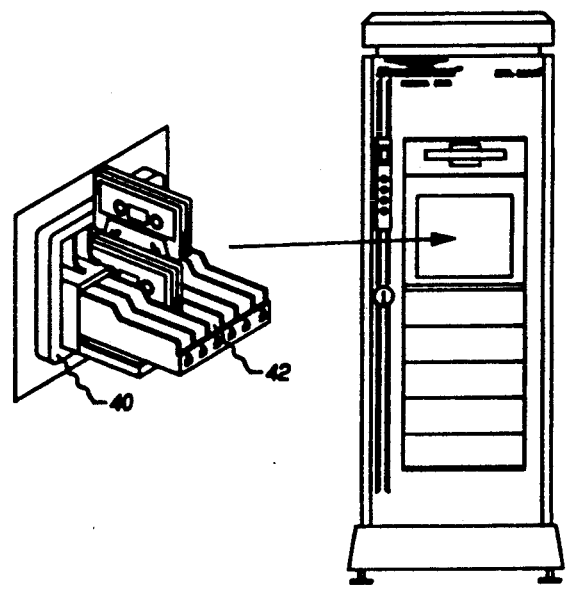
FIG. 1b is a pictorial representation of a multicassette feeder as used in the second embodiment of the invention.

As seen in FIG. 1b, a second embodiment of the invention uses an automatic feeder 40 to operate in a batch mode. The automatic feeder 40 as used in the preferred second embodiment is a modified version of cassette loader/feeders that are well known to the art, will load a plurality of patient ECG recordings 50 into the Triage TM system 10 to be scanned. Each of the patient recordings are first labeled with a bar code to identify the patient, any patient medication, the patient's doctor and the date the recording was made. Each of the patient recordings identification code is then entered into the scanner by the keyboard means 12. The patient recordings, which in the preferred embodiment would be tape cassettes, are loaded into the drawer 42 on the automatic feeder 40. The recordings are then sequentially tested by the Triage TM scanning method and apparatus to identify those recordings containing no significant abnormalities. As in the previous embodiment, the operator presets the thresholds used to identify significant abnormalities. Here batch refers to a mode of operation in which several ECG records are to be analyzed sequentially without an operator intervention. Multiple records of patient ECG data are loaded into a scanner that has the means to scan each of the records sequentially. Depending on the mode that the operator chooses, the operator may or may not be allowed to interact with the test while in progress and view the results when a threshold has been exceeded. Via operator selection tests may be run as shown in the preferred embodiment of the invention. Here, the operator must select either automatic, confirm or Triage TM modes of operation when prompted for termination after a threshold has been exceeded. Alternatively, operation in the batch mode may be selected to allow the tests to continue running if threshold is exceeded. Here, the operator may only view a report on the results of all the tests made on the recordings prior deciding which recordings contain no significant abnormalities. Thus, by batch mode loading of patient ECG recordings, it is possible to provide a unique Triage TM analysis to a plurality of ECG recordings that is fully automated. It is possible to eliminate as many as 30% of a plurality of recordings employing automatic recording feeders and using automated Triage TM thresholding techniques.

A third embodiment of this invention would use digitally recorded ECG data in place of the analog recorded ECG data as disclosed in the preferred embodiment. Here digital recorded ECG data can be digitally recorded on tape or using means for solid state recording with the computer system 10.

It is obvious to those skilled in the art that the above mentioned embodiments can be modified without departing from the spirit and scope of the invention. The embodiments as described herein are not, therefore, to be considered as illustrating all possible variations of the invention, and all changes that are embraced by the claims of the invention are therefore considered equivalent to the embodiments of the invention as disclosed and claimed herein.

What is claimed is:

1. An apparatus used to provide for automatic screening of recorded electrocardiographic (ECG) signals to identify recordings containing no clinically significant abnormalities thereby eliminating those ECG recordings from the requirement of being manually analyzed, consisting of:
   computational means, said computational means including playback means capable of inputting recorded ECG signals as a set of digital ECG signals that can be assessed by said computational means;
   means for arrhythmia analyzing, contained within said computational means, capable of taking said set of digital ECG signals to provide, therefrom, assessments of said recorded ECG data as being a member of one of a group of categories, said group of categories including a ventricular ectopic, a superventricular ectopic, an ST index, an artifact, or an unknown;
   accumulation means contained within said computational means to store a total number of occurrences of each of said categories;
   means responsive to said accumulation means for automatically detecting significant abnormalities in said digital ECG signals, and responding thereto.

2. The invention of claim 1 wherein said means responsive to said accumulation means includes interruption means contained within said computational means, said interruption means capable of generating a program interruption when a predetermined threshold for any of said categories is exceeded, said program interruption occurring when an accumulation of any of said categories exceeds said predetermined threshold.

3. The invention of claim 2 wherein said interruption means further includes iterative means to repeatedly test each set of said digital ECG signals using said means for arrhythmia analyzing to determined whether any of said categories exceeds said predetermined threshold, thereby, determining if clinically significant recorded abnormalities exist.

4. The invention disclosed in claim 1 wherein said group of categories also includes a confidence level, wherein said confidence level is a measure of difficulty in confidently assuming that said group of categories determined by said arrhythmia analyzer have been correctly classified.

5. The invention of claim 2 wherein said interruption means includes an additional threshold for a VE grade and a SVE grade, wherein each of said grades provides for a specific test and both of said grades being selected from a predetermined group.

6. A method of automatically screening recorded electrocardiographic data to eliminate recordings not containing clinically significant abnormalities without requiring manual inspection comprising the steps of:
   providing recorded ECG data as a set of digital ECG signals into a digital computer to be processed;
   arrhythmia analyzing said set of digital ECG signals to access ECG events, provide for beat detection and obtain a summary view of morphology classification;
   grouping events from said arrhythmia analyzing by assessing said summary view of morphology classification to create a group of categories, said categories including individual assessments of ECG data being either an artifact, a ventricular ectopic, a superventricular ectopic, or an unknown event;
   providing for a confidence level that each of said morphology classifications is as classified and said categories are properly grouped;
   accumulating a total number of occurrences of each of said categories over a predetermined set of time periods;
   automatically determining whether clinically significant abnormalities are contained within recorded electrocardiographic data by employing means responsive to said total number of occurrences for each said categories within each of said predetermined time periods.

7. The method of claim 6 wherein the step of automatically determining further comprises the steps of:
   comparing each of said total number of occurrences from said accumulating step against a predetermined number of occurrences for said category during said predetermined time period;
   reporting said means responsive to said total number of occurrences when said total number of occurrences for any of said categories has exceeded a predetermined number for the last hour, or whether said total number of occurrences for any of said categories has exceeded a predetermined number in total, or whether a predetermined grade for any of said categories has been reached; and performing the foregoing steps iteratively on each detected beat to determine whether recordings contain clinically significant abnormalities, thus creating a basis for deciding which recordings may be excused from manual analysis.

8. The method of claim 6 wherein the steps of grouping and providing said confidence level further comprises the steps of:

representing as a set of vectors each of said detected beats in a multidimensional Euclidian space;

storing said set of vectors for each of said detected beats;

comparing said set of vectors for each of said detected beats with said sets of vectors derived from other said detected beats;

creating a set of groups according to results obtained from said comparing step; and generating a confidence level that said groups are properly formed.

9. The method of claim 6 where the step of grouping and accumulating further include the step of determining a ventricular ectopic (VE) grade as being of one of seven grades including: (1) no VE activity; (2) between one and 30 VE events within the span of sixty minutes; (3) more than 30 VE events in the span of sixty minutes; (4) a VE pair (two consecutive beats being classified as VE) occurring; (5) an intraventricular run of more than three VE's occurring with a heart rate of less than 95 beats per minute; (6) a VE triplet (three consecutive beats classified as VE with a heart rate of more than 95 beats per minute) occurring; or a VT run of 4 or more VE's.

10. The method of claim 6 wherein the steps of grouping and accumulating further include determining a grade of super ventricular ectopics as: (1) no SVE activity; (2) 1 to 30 SVE's in a sixty minute span; (3) more than 30 SVE's occurring within an hour; (4) a SVE pair; (5) TBD; (6) SVT run of three to five; (7) SVT run of more than five; or (8) pause.

11. A method of analyzing recorded electrocardiographic (ECG) signals to determine the presence of clinically significant abnormalities in heart arrhythmia or heartbeat morphology comprising the steps of:

providing a digital computer with recorded ECG data as a set of digital ECG signals to be used for digital processing;

forming vector representations in multidimensional Euclidian space of heart arrhythmia and heartbeat morphology from said recording of digital ECG data;

generating a group of categories related to heart arrhythmia and heartbeat morphology from said vector representations;

accumulating a set of total occurrences for each of said group of categories over a predetermined set of time intervals;

providing a predetermined set of thresholding parameters having members that correspond to those members contained in said set of total occurrences; and comparing said set of total occurrences for each of said categories with said predetermined set of thresholding parameters to determine the presence of clinically significant abnormalities in heart arrhythmia or heartbeat morphology.

12. The method of claim 11 wherein the step of comparing said accumulation of occurrences for each of said categories with said thresholding parameter consists of iteratively testing each member of said set of digital data for occurrences of each of said categories to determine which recordings contain significant abnormalities.

13. The method of claim 11 wherein the step of forming vector representations further comprises the step of transforming said set of digital ECG signals by means of a KLT mathematical transform.

14. The method of claim 11 wherein the step of generating said group of categories further includes the steps of:

extracting feature vectors from detected beats;

creating clusters of beats having similar feature vectors;

comparing clusters for similarities;

classifying clusters; and detecting arrhythmia episodes by thresholding the number of beats in clusters.

15. The method of claim 11 wherein the step of comparing further comprises comparing members of said set of total number of occurrences relating to VE, SVE, VE grade, SVE grade and artifacts, against respective members from said predetermined set of thresholding parameters, each of said thresholding parameters being individually adjustable by the user.

16. A system for analyzing recorded electrocardiographic data to determine the presence of clinically significant data comprising:

a digital computer having loading means, said loading means capable of individual insertion and removal, of each of a plurality of patient recordings into said digital computer;

digitizing means, contained within said computer, capable of making data from said patient recordings available to said digital computer in a digital format;

means for digitally processing said patient recordings in said digital format, contained within said digital computer, said means for digitally processing capable of performing an arrhythmia analysis;

means for categorizing results achieved through said arrhythmia analysis;

means responsive to said means for categorizing for automatically determining which of said plurality of patient recordings contain no clinically significant data and, therefore, may be excused from the requirement of manual analysis.

17. The invention of claim 16 wherein said arrhythmia analysis further consists of:

means for detecting valid heartbeats;

means for extracting a feature vector from each of said valid heartbeats;

means for providing an analysis of said feature vectors to determine the clinical significance of abnormalities contained within said feature vectors.

18. The invention of claim 16 wherein said means responsive to said means for categorizing includes interruption means contained within said computational means, said interruption means capable of generating a program interruption when a predetermined threshold for any of said categories is exceeded, said program interruption occurring when an accumulation of any of said categories exceeds said predetermined threshold.

19. The invention of claim 18 wherein said interruption means further includes iterative means to repeatedly test each set of said digital ECG signals using said means for arrhythmia analyzing to determine whether any of said categories exceeds said predetermined threshold, thereby determining if clinically significant recorded abnormalities exists.

20. The invention of claim 16 wherein said means responsive to said means for categorizing consists of identification means capable of placing on said patient recordings results that indicate if there is clinically significant cardiac abnormalities contained on said recording.

21. The invention of claim 16 wherein said means responsive to said means for categorizing is a display mechanism that is part of said computer, said display mechanism operating to alert operators of clinically significant cardiac abnormalities present on said patient recordings.

* * * * *